(12) United States Patent
Blalock et al.

(10) Patent No.: US 11,327,469 B2
(45) Date of Patent: May 10, 2022

(54) METHODS, SYSTEMS, AND COMPUTER PROGRAM PRODUCTS FOR MANAGING MULTIPLE DRUG PRODUCT PACKAGING SYSTEMS USING A COMMON DATABASE MANAGEMENT SYSTEM

(71) Applicant: PARATA SYSTEMS, LLC, Durham, NC (US)

(72) Inventors: Collin D. Blalock, Cary, NC (US); Brian Cristobal, Raleigh, NC (US); Gary M. Owen, Wake Forest, NC (US); Mark Longley, Raleigh, NC (US)

(73) Assignee: PARATA SYSTEMS, LLC, Durham, NC (US)

( * ) Notice: Subject to any disclaimer, the term of this patent is extended or adjusted under 35 U.S.C. 154(b) by 107 days.

(21) Appl. No.: 16/694,198

(22) Filed: Nov. 25, 2019

(65) Prior Publication Data
US 2020/0085685 A1 Mar. 19, 2020

Related U.S. Application Data

(63) Continuation of application No. 15/633,175, filed on Jun. 26, 2017, now Pat. No. 10,492,987.

(51) Int. Cl.
*G05B 19/418* (2006.01)
*B65B 5/10* (2006.01)
(Continued)

(52) U.S. Cl.
CPC ............ *G05B 19/4183* (2013.01); *A61J 1/00* (2013.01); *A61J 1/03* (2013.01); *A61J 1/035* (2013.01); *A61J 1/06* (2013.01); *A61J 1/065* (2013.01); *A61J 1/10* (2013.01); *B65B 1/02* (2013.01); *B65B 1/04* (2013.01); *B65B 5/103* (2013.01); *B65D 83/04* (2013.01); *G05B 19/418* (2013.01);
(Continued)

(58) Field of Classification Search
CPC .... A61J 1/00; A61J 1/03; B65B 5/103; G05B 19/4183
See application file for complete search history.

(56) References Cited

U.S. PATENT DOCUMENTS 5,715,660 A 2/1998 Balentine
6,311,743 B1 * 11/2001 Baroncini ............... B65B 5/103
141/131
(Continued)

FOREIGN PATENT DOCUMENTS

WO 2015095738 6/2015

OTHER PUBLICATIONS

Canadian Exam Report corresponding to CA 2,971,927; dated Oct. 22, 2021 (4 pages).

*Primary Examiner* — Thomas Randazzo
(74) *Attorney, Agent, or Firm* — Myers Bigel, P.A.

(57) ABSTRACT

A method includes performing, by a processor: providing a database that contains records corresponding to a plurality of drug product packaging systems, the records in the database being accessible through a common database management system, receiving a packaging order for at least one drug product, evaluating at least one criterion for fulfilling the packaging order, and identifying one of the plurality of drug product packaging systems to package the at least one drug product based on evaluating the at least one criterion.

20 Claims, 5 Drawing Sheets

(51) Int. Cl.
  *A61J 1/00*      (2006.01)
  *A61J 1/03*      (2006.01)
  *B65B 1/04*      (2006.01)
  *B65D 83/04*     (2006.01)
  *A61J 1/10*      (2006.01)
  *A61J 1/06*      (2006.01)
  *G16H 40/20*     (2018.01)
  *G16H 20/13*     (2018.01)
  *G06Q 10/08*     (2012.01)
  *B65B 1/02*      (2006.01)
  *G06F 16/00*     (2019.01)

(52) U.S. Cl.
  CPC .......... *G06Q 10/087* (2013.01); *G16H 20/13* (2018.01); *G16H 40/20* (2018.01); *G06F 16/00* (2019.01)

(56) References Cited

U.S. PATENT DOCUMENTS

| | | | |
|---|---|---|---|
| 6,471,089 B2 | 10/2002 | Liff et al. | |
| 6,769,228 B1 * | 8/2004 | Mahar | B65B 61/20 53/155 |
| 8,321,236 B2 | 11/2012 | Goodall et al. | |
| 8,571,886 B2 | 10/2013 | Chudy et al. | |
| 8,666,780 B2 | 3/2014 | Berkelhamer et al. | |
| 8,712,582 B1 * | 4/2014 | Luciano, Jr. | G06Q 10/087 700/236 |
| 8,768,498 B2 * | 7/2014 | Hermann | G05B 23/0251 700/99 |
| 2002/0103573 A1 | 8/2002 | Fellows et al. | |
| 2004/0215521 A1 | 10/2004 | Crisp, III | |
| 2005/0171813 A1 | 8/2005 | Jordan | |
| 2006/0025884 A1 * | 2/2006 | Henkel | B65B 5/103 700/216 |
| 2007/0135944 A1 * | 6/2007 | Schmid | G05B 23/0272 700/83 |
| 2008/0071648 A1 | 3/2008 | Kim | |
| 2009/0037209 A1 * | 2/2009 | Schulze | G06Q 10/083 705/330 |
| 2010/0241270 A1 * | 9/2010 | Eliuk | B01F 13/1072 700/216 |
| 2011/0137447 A1 * | 6/2011 | Hermann | G05B 23/0251 700/108 |
| 2012/0173254 A1 | 7/2012 | Korhnak et al. | |
| 2012/0173391 A1 | 7/2012 | Korhnak et al. | |
| 2013/0097975 A1 * | 4/2013 | Bailey | B65G 47/08 53/473 |
| 2013/0246026 A1 * | 9/2013 | Ceglia | G05B 17/02 703/6 |
| 2013/0246037 A1 * | 9/2013 | Ceglia | G05B 23/0216 703/13 |
| 2014/0148945 A1 * | 5/2014 | Cunningham | G07F 11/44 700/236 |
| 2014/0262883 A1 * | 9/2014 | Devouassoux | A61B 50/30 206/364 |
| 2015/0120010 A1 * | 4/2015 | Hashimoto | H04L 41/24 700/83 |
| 2015/0286799 A1 | 10/2015 | Padmani et al. | |
| 2016/0203445 A1 * | 7/2016 | Honsinger | G06Q 10/063114 705/7.15 |
| 2017/0015445 A1 * | 1/2017 | Holmes | G07F 11/165 |
| 2017/0235292 A1 * | 8/2017 | Wernersbach | G05B 19/0428 700/81 |
| 2017/0247161 A1 * | 8/2017 | Balthes | G01N 15/08 |
| 2018/0022493 A1 * | 1/2018 | Lamb | G05B 19/188 700/103 |
| 2018/0095937 A1 * | 4/2018 | Hirayama | G06F 7/02 |

* cited by examiner

METHODS, SYSTEMS, AND COMPUTER PROGRAM PRODUCTS FOR MANAGING MULTIPLE DRUG PRODUCT PACKAGING SYSTEMS USING A COMMON DATABASE MANAGEMENT SYSTEM

RELATED APPLICATION

The present application is a continuation of and claims priority to U.S. patent application Ser. No. 15/633,175, filed Jun. 26, 2017, the disclosure of which is hereby incorporated herein by reference in its entirety.

BACKGROUND

The present disclosure relates generally to the dispensing of drug products, and, in particular, to methods, systems, and computer program products for managing multiple drug product packaging systems.

Drug product packaging systems may be used in facilities, such as pharmacies, hospitals, long term care facilities, and the like to dispense medications to fill prescriptions. These drug product packaging systems may include systems designed to package medications in various container types including vials and strip packaging. Strip packaging is a type of packaging wherein medications are packaged in individual pouches for administration on a specific date and, in some cases, at a specific time. Typically, these pouches are removably joined together and often provided in rolls. The pouches can be separated from the roll when needed. Although a facility may have multiple drug product packaging systems in operation, the packaging systems are typically managed individually with each packaging system having its own database associated therewith.

SUMMARY

In some embodiments of the inventive concept, a method comprises, performing by a processor: providing a database that contains records corresponding to a plurality of drug product packaging systems, the records in the database being accessible through a common database management system, receiving a packaging order for at least one drug product, evaluating at least one criterion for fulfilling the packaging order, and identifying one of the plurality of drug product packaging systems to package the at least one drug product based on evaluating the at least one criterion.

In other embodiments of the inventive subject matter, a system comprises a processor and a memory coupled to the processor and comprising computer readable program code embodied in the memory that is executable by the processor to perform: providing a database that contains records corresponding to a plurality of drug product packaging systems, the records in the database being accessible through a common database management system, receiving a packaging order for at least one drug product, evaluating at least one criterion for fulfilling the packaging order, and identifying one of the plurality of drug product packaging systems to package the at least one drug product based on evaluating the at least one criterion.

In further embodiments of the inventive subject matter, a computer program product comprises a tangible computer readable storage medium comprising computer readable program code embodied in the medium that is executable by a processor to perform: providing a database that contains records corresponding to a plurality of drug product packaging systems, the records in the database being accessible through a common database management system, receiving a packaging order for at least one drug product, evaluating at least one criterion for fulfilling the packaging order, and identifying one of the plurality of drug product packaging systems to package the at least one drug product based on evaluating the at least one criterion.

It is noted that aspects described with respect to one embodiment may be incorporated in different embodiments although not specifically described relative thereto. That is, all embodiments and/or features of any embodiments can be combined in any way and/or combination. Moreover, other methods, systems, articles of manufacture, and/or computer program products according to embodiments of the inventive subject matter will be or become apparent to one with skill in the art upon review of the following drawings and detailed description. It is intended that all such additional systems, methods, articles of manufacture, and/or computer program products be included within this description, be within the scope of the present inventive subject matter, and be protected by the accompanying claims. It is further intended that all embodiments disclosed herein can be implemented separately or combined in any way and/or combination.

BRIEF DESCRIPTION OF THE DRAWINGS

Other features of embodiments will be more readily understood from the following detailed description of specific embodiments thereof when read in conjunction with the accompanying drawings, in which.

DETAILED DESCRIPTION

Figure 1:
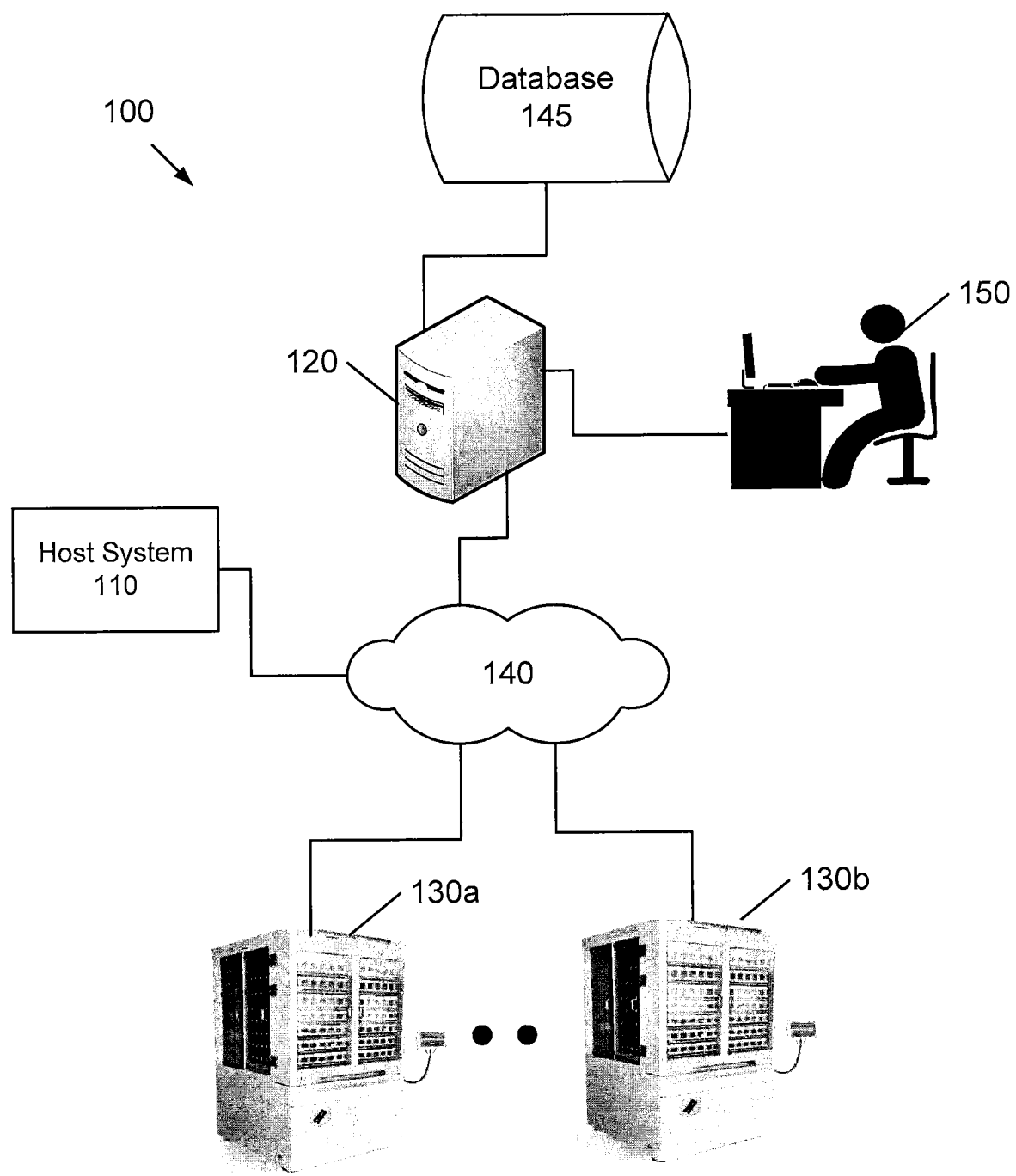
FIG. 1 is a block diagram that illustrates a communication network including a packaging system management server for managing multiple drug product packaging systems using a common database management system in accordance with some embodiments of the inventive concept.

In the following detailed description, numerous specific details are set forth to provide a thorough understanding of embodiments of the present disclosure. However, it will be understood by those skilled in the art that the present invention may be practiced without these specific details. In some instances, well-known methods, procedures, components and circuits have not been described in detail so as not to obscure the present disclosure. It is intended that all embodiments disclosed herein can be implemented separately or combined in any way and/or combination. Aspects described with respect to one embodiment may be incorporated in different embodiments although not specifically described relative thereto. That is, all embodiments and/or features of any embodiments can be combined in any way and/or combination.

As used herein, the term "data processing facility" includes, but it is not limited to, a hardware element, firmware component, and/or software component. A data processing system may be configured with one or more data processing facilities.

The term "drug product packaging system," as used herein, refers to any type of pharmaceutical dispensing system including, but not limited to, automated systems that fill vials, containers, pouch, or the like with drug product, and semi-automated systems that fill vials, containers, pouches or the like with drug product.

The terms "pharmaceutical" and "medication," as used herein, are interchangeable and refer to medicaments prescribed to patients.

The term "drug product" refers to any type of medicament that can be packaged within a vial, container, pouch, or the like by automated and semi-automated drug product packaging systems including, but not limited to, pills, capsules, tablets, caplets, gel caps, lozenges, and the like.

Some embodiments of the inventive concept stem from a realization that managing drug product packaging systems on an individual basis with separate database management systems corresponding to each respective packaging system may be inefficient. For example, drug product dispensing canisters are registered with a single packaging system and are not shared between packaging systems because of concerns with corruption of inventory data. Similarly, production reports, billing reports, and the like are run for each individual packaging system requiring separate processing to aggregate the individual reports to obtain a facility-wide viewpoint. Incoming drug product packaging orders are also routed to packaging systems manually as a central routing point for all packaging systems is not available. According to some embodiments of the inventive concept, a common database management system may be used to manage records for multiple drug product packaging systems. This may allow for various performance criteria to be defined enabling centralized routing of packaging orders to the drug product packaging system that may fulfill the order in a more efficient manner. Moreover, because all of the drug product packaging systems are managed through a common database management system, reports can be run both on an individual packaging system basis as well as an aggregate basis that encompasses all of the packaging systems. The use of a common database management system may also allow drug product dispensing canisters to be registered with multiple ones of the drug product packaging systems and shared therebetween without corrupting inventory records for the various packaging systems as they are part of the same database and managed together.

Referring to FIG. 1, a communication network 100, in accordance with some embodiments of the present inventive concept, comprises a host system 110, a packaging system management server 120, and multiple drug product packaging systems 130a and 130b that are coupled via a network 140 as shown. The network 140 may be a global network, such as the Internet or other publicly accessible network. Various elements of the network may be interconnected by a wide area network, a local area network, an Intranet, and/or other private network, which may not be accessible by the general public. Thus, the network 150 may represent a combination of public and private networks or a virtual private network (VPN).

The host system 110 may be configured to manage and fill prescriptions for customers. The host system 110 may be associated with a variety of types of facilities, such as pharmacies, hospitals, long term care facilities, and the like. The packaging system management server 120 may be configured to manage the operation of the drug product packaging systems 130a and 130b. For example, the packaging system management server 120 may be configured to receive packaging orders from the pharmacy host system 110 and to identify which of the drug product packaging systems 130a and 130b should be used to package particular individual orders or batches of orders. In addition, the packaging system management server 120 may be configured to manage the operations of the drug product packaging systems 130a and 130b. For example, the packaging system management server 120 may be configured to manage the inventory of drug product available through each of the drug product packaging systems 130a and 130b, to manage the drug product dispensing canisters assigned or registered to one or more of the drug product packaging systems 130a and 130b, and/or to manage reports regarding the status (e.g., assignment, completion, etc.) of packaging orders, drug product inventory, order billing, and the like. A user 150, such as a pharmacist or pharmacy technician, may communicate with the packaging system management server 120 using any suitable computing device via a wired and/or wireless connection. Although the user 150 is shown communicating with the packaging system management server 120 via a direct connection in FIG. 1, it will be understood that the user 150 may communicate with the packaging system management server 120 via one or more network connections. The user 150 may interact with the packaging system management server 120 to approve or override various recommendations made by the packaging system management server 120 in operating the drug product packaging systems 130a and 130b. The user 150 may also initiate the running of various reports as described above for the drug product packaging systems 130a and 130b. Although only two drug product packaging systems 130a and 130b are shown in FIG. 1, it will be understood that more than two drug product packaging systems may be managed using a common database management system in accordance with various embodiments of the inventive concept.

The packaging system management server 120 uses a common database management system to manage a database 145 that contains records corresponding to drug product packaging systems 130a and 130b. According to some embodiments of the inventive concept, a common database management system and database may be used to store records for all of the drug product packaging systems of the same type. For example, some drug product packaging systems may be configured to package one or more drug products in pouches formed in a container strip. Other drug product packaging systems may be configured to package one or more drug products in a vial. Thus, a common database management system and database may be used for all of the drug product packaging systems that package one or more drug products in a vial and a common database management system and database may be used for all of the drug product packaging systems that package one or more drug products in pouches formed in a container strip. In some embodiments, the database 145 may be a relational database, such as a Structured Query Language (SQL) or DB2 database. It will be understood, however, that embodiments of the inventive concept are not limited in their application to a relational database model as other database models, such as, but not limited to, a flat database model, a hierarchical database model, a network database model, an object-relational database model, and a star schema database model may also be used. It will be appreciated that in accordance with various embodiments of the inventive concept, the packaging system management server 120 may be implemented as a single server, separate servers, or a network of servers either co-located in a server farm, for example, or located in different geographic regions.

Although FIG. 1 illustrates an exemplary communication network for managing multiple drug product packaging systems using a common database management system, it will be understood that embodiments of the inventive subject matter are not limited to such configurations, but are intended to encompass any configuration capable of carrying out the operations described herein.

Figure 2:
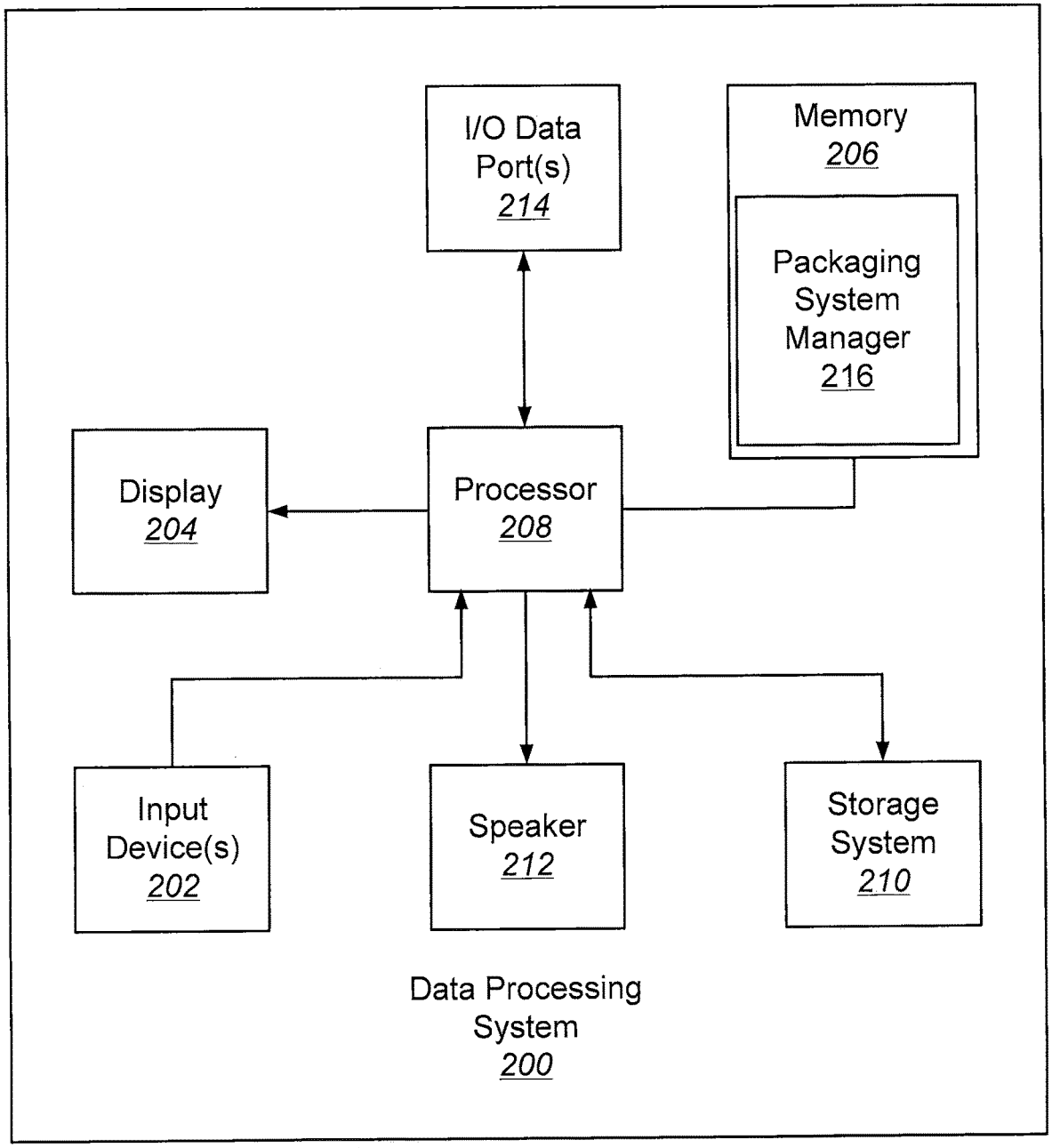
FIG. 2 illustrates a data processing system that may be used to implement the packaging system management server of FIG. 1 in accordance with some embodiments of the inventive concept.

Referring now to FIG. 2, a data processing system 200 that may be used to implement the packaging system management server 120 of FIG. 1, in accordance with some embodiments of the inventive concept, comprises input device(s) 202, such as a keyboard or keypad, a display 204, and a memory 206 that communicate with a processor 208. The data processing system 200 may further include a storage system 210, a speaker 212, and an input/output (I/O) data port(s) 214 that also communicate with the processor 208. The storage system 210 may include removable and/or fixed media, such as floppy disks, ZIP drives, hard disks, or the like, as well as virtual storage, such as a RAMDISK. The I/O data port(s) 214 may be used to transfer information between the data processing system 200 and another computer system or a network (e.g., the Internet). These components may be conventional components, such as those used in many conventional computing devices, and their functionality, with respect to conventional operations, is generally known to those skilled in the art. The memory 206 may be configured with a packaging system management module 216 that may provide functionality that may include, but is not limited to, managing multiple drug product packaging systems using a common database management system in accordance with some embodiments of the inventive concept.

Figure 3:
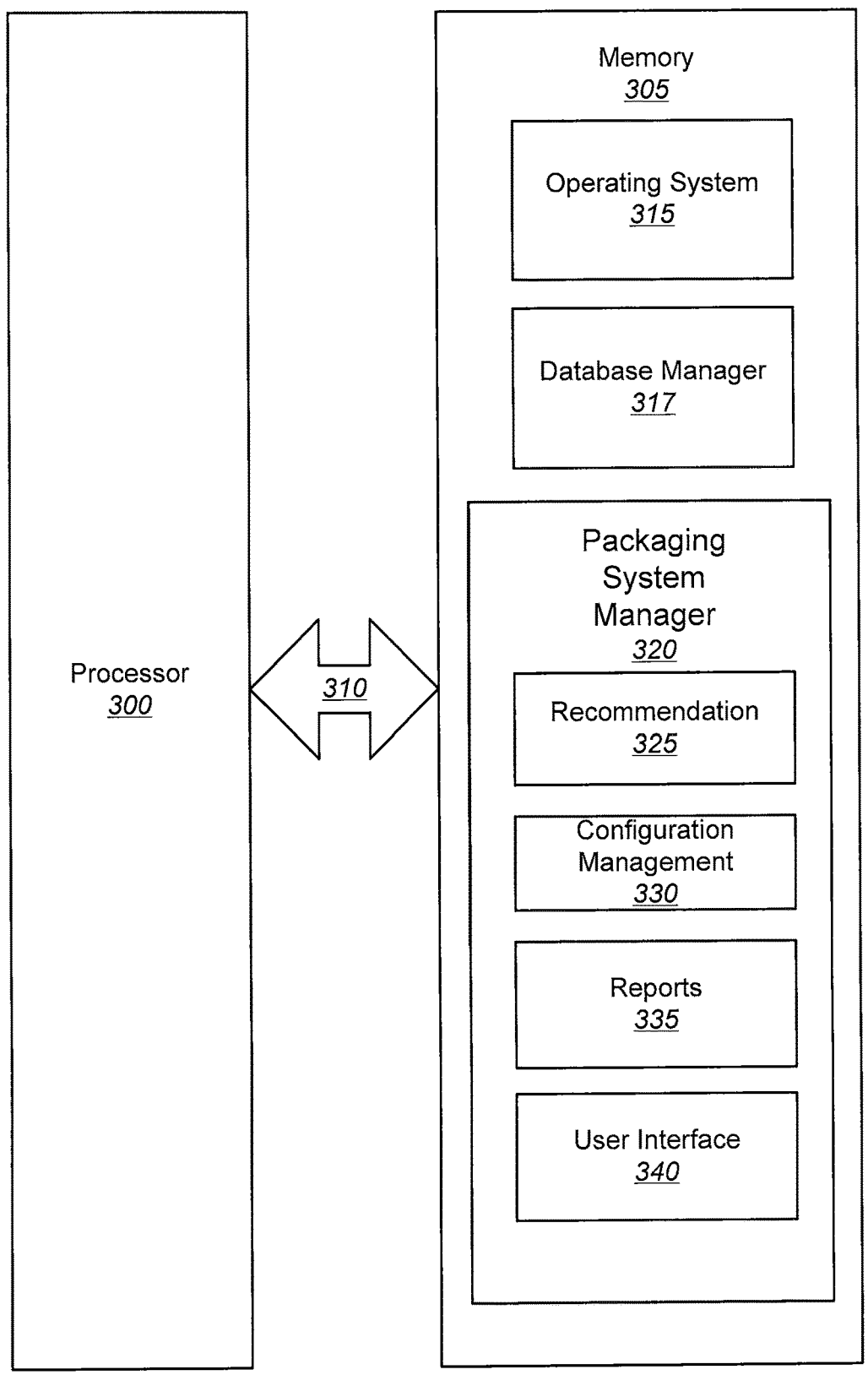
FIG. 3 is a block diagram that illustrates a software/hardware architecture for use in a packaging system management server for managing multiple drug product packaging systems using a common database management system in accordance with some embodiments of the inventive concept.

FIG. 3 illustrates a processor 300 and memory 305 that may be used in embodiments of data processing systems, such as the packaging system management server 120 of FIG. 1 and the data processing system 200 of FIG. 2, respectively, for managing multiple drug product packaging systems using a common database management system in accordance with some embodiments of the inventive concept. The processor 300 communicates with the memory 305 via an address/data bus 310. The processor 300 may be, for example, a commercially available or custom microprocessor. The memory 305 is representative of the one or more memory devices containing the software and data used for managing multiple drug product packaging systems using a common database management system in accordance with some embodiments of the inventive concept. The memory 305 may include, but is not limited to, the following types of devices: cache, ROM, PROM, EPROM, EEPROM, flash, SRAM, and DRAM.

As shown in FIG. 3, the memory 305 may contain three or more categories of software and/or data: an operating system 315, a database manager 317, and a packaging system manager module 320. In particular, the operating system 315 may manage the data processing system's software and/or hardware resources and may coordinate execution of programs by the processor 300. The database manager 316 may comprise the database management system (DBMS) software, which is used to facilitate the definition, creation, querying, update, and administration of a database, such as the database 145 of FIG. 1. The packaging system manager module 320 may comprise a recommendation module 325, a configuration management module 330, a reports module 335, and a user interface module 340.

The recommendation module 325 may be configured to receive a packaging order for one or more drug products from a host system, such as the host system 110 of FIG. 1. The packaging order may be placed in a queue with one or more additional packaging orders. In some embodiments, a priority may be assigned to the packaging order such that the recommendation module 325 removes packaging orders from the queue for evaluation based on the priority assigned to the packaging order and/or the length of time that the packaging order has been in the queue. For example, in some embodiments, the recommendation module may remove a packaging order from the queue for evaluation that has been in the queue the longest amount of time. In other embodiments, priority designations may be assigned to packaging orders that may allow the packaging order to be evaluated in advance of other packaging orders that have been in the queue for a longer period of time. In some embodiments, a particular priority level may allow a packaging order to be evaluated ahead of all other packaging orders that have been in the queue for less than a time threshold, but not before packaging orders that have been in the queue for longer than the time threshold. In still other embodiments, a particular priority level may allow a packaging order to be evaluated ahead of all packaging orders that are of a lower priority irrespective of how long any of the packaging orders have been in the queue.

The recommendation module 325 may be further configured to remove packaging orders from the queue and to evaluate one or more criterion for fulfilling the packaging order. One of the drug product packaging systems 130*a*, 130*b* may then be identified to package the one or more drug products contained in the packaging order based on the evaluation.

The configuration management module 330 may be configured to manage the settings of the drug product packaging systems 130*a*, 130*b* and to update this information in the database 145 using the database manager 317. The settings may include various operating settings for the mechanical/robotic components of the drug product packaging systems 130*a*, 130*b*. The configuration management module 330 may also manage the inventory of drug product stored in the various dispensing canisters installed in each of the drug product packaging systems 130*a*, 130*b* as well as drug product available in spare dispensing canisters that have been registered with one or more of the drug packaging systems 130*a*, 130*b*, but are not currently installed. Because multiple drug product packaging systems 130*a*, 130*b* can be managed using a common database management system, spare dispensing canisters can be registered across multiple drug product packaging systems 130*a*, 130*b* and interchanged therebetween. In some embodiments where the multiple drug packaging systems 130*a*, 130*b* are of the same type (e.g., vial or pouch/strip), but the different drug packaging systems 130*a*, 130*b* have different dispensing canister capacities where there is not a one-to-one correspondence between dispensing canister positions in each of the drug packaging systems 130*a*, 130*b*, the dispensing canisters may be registered solely with a single drug product packaging system 130*a*, 130*b* and dispensing canisters are not swapped between each other. In general, spare or reserve canisters may be maintained and registered to one or multiple drug packaging systems 130*a*, 130*b* to provide reserves for various drug products whose canisters are installed in one or more particular drug packaging systems 130*a*, 130*b* or, in some embodiments, as additional drug products even when all the positions are occupied for the drug packaging system(s) 130*a*, 130*b*, that the spare canister(s) are registered with.

The reports module 335 may be configured to create and generate reports regarding the status (e.g., assignment, completion, etc.) of packaging orders, drug product inventory, order billing, and the like based on records stored in the database 145 for a particular group of drug product packaging systems 130*a*, 130*b*.

The user interface module 340 may be configured to display recommendations for assigning one or more drug products for packaging to a particular drug product packaging system 130*a*, 130*b*, which is generated by the recommendation module 325, to a user 150. In some embodiments, a default operational mode may be selected and the recommended packaging assignment may be selected automatically and routed to the appropriate drug product packaging system 130*a*, 130*b* without any input from the user with respect to the particular packaging order(s). In other embodiments, the user 150 may accept or override the recommendation through, for example, a graphical user interface. The user interface module 340 may also be configured to facilitate the initiation of running various reports generated through the reports module 335.

Although FIG. 3 illustrates hardware/software architectures that may be used in data processing systems, such as the packaging system management server 120 of FIG. 1 and the data processing system 200 of FIG. 2, respectively, for managing multiple drug product packaging systems using a common database management system in accordance with some embodiments of the inventive concept, it will be understood that the present invention is not limited to such a configuration but is intended to encompass any configuration capable of carrying out operations described herein.

Computer program code for carrying out operations of data processing systems discussed above with respect to FIGS. 1-3 may be written in a high-level programming language, such as Python, Java, C, and/or C++, for development convenience. In addition, computer program code for carrying out operations of the present invention may also be written in other programming languages, such as, but not limited to, interpreted languages. Some modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller.

Moreover, the functionality of the packaging system management server 120 of FIG. 1, the data processing system 200 of FIG. 2, and the hardware/software architecture of FIG. 3 may each be implemented as a single processor system, a multi-processor system, a multi-core processor system, or even a network of stand-alone computer systems, in accordance with various embodiments of the inventive concept. Each of these processor/computer systems may be referred to as a "processor" or "data processing system."

The data processing apparatus of FIGS. 1-3 may be used to facilitate the management of multiple drug product packaging systems using a common database management system according to various embodiments described herein. These apparatus may be embodied as one or more enterprise, application, personal, pervasive and/or embedded computer systems and/or apparatus that are operable to receive, transmit, process and store data using any suitable combination of software, firmware and/or hardware and that may be standalone or interconnected by any public and/or private, real and/or virtual, wired and/or wireless network including all or a portion of the global communication network known as the Internet, and may include various types of tangible, non-transitory computer readable media. In particular, the memory 206 coupled to the processor 208 and the memory 305 coupled to the processor 300 include computer readable program code that, when executed by the respective processors, causes the respective processors to perform operations including one or more of the operations described herein with respect to FIG. 4.

Figure 4:
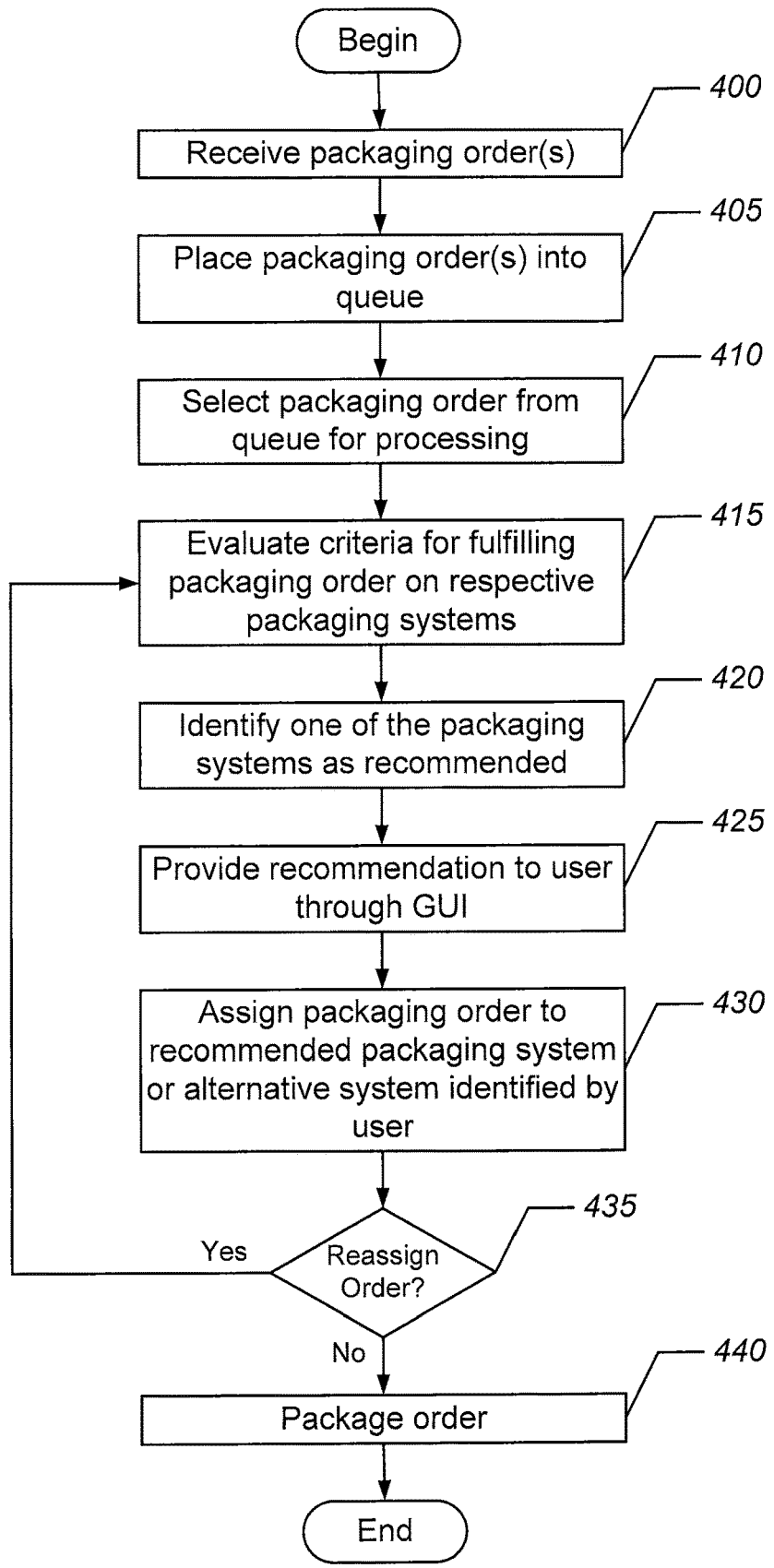
FIG. 4 is a flowchart diagram that illustrates operations for managing multiple drug product packaging systems using a common database management system in accordance with some embodiments of the inventive subject matter.

FIG. 4 is a flowchart that illustrates operations for managing multiple drug product packaging systems using a common database management system in accordance with some embodiments of the inventive concept. Operations begin at block 400 where recommendation module 325 receives a packaging order for one or more drug products from the host system 110. A validation check may be performed to ensure that each of the one or more drug products corresponds to a valid National Drug Code (NDC) that is inventoried and available for dispensation through at least one of the drug product packaging systems 130*a*, 130*b*. If the validation check fails, the packaging order may be rejected as an invalid order. If the validation check is successful, the packaging order may be placed into a queue comprising a plurality of packaging orders at block 405. At block 410, the recommendation module 325 may select the packaging order from the queue at a time based on a priority assigned to the packaging order and/or a length of time the packaging order has been in the queue. One or more criterion may then be evaluated for fulfilling the packaging order at block 415. These criteria may be applied to the plurality of drug product packaging systems 130*a*, 130*b* and a recommendation made regarding which of the drug product packaging systems 130*a*, 130*b* may be preferred in packaging the one or more drug products comprising the packaging order.

In some embodiments of the inventive concept, the evaluation criteria may include, but are not limited to, 1) an idle or active status for the respective one of the plurality of drug product packaging systems 130*a*, 130*b*, 2) a number of the one or more drug products that does not have a dispensing canister associated therewith for the respective one of the plurality of drug product packaging systems 130*a*, 130*b*, 3) an amount of the one or more drug products that is contained in at least one dispensing canister, respectively, for the respective one of the plurality of drug product packaging systems 130*a*, 130*b*, 4) an amount of the one or more drug products that is contained in at least one dispensing canister, respectively, that is associated with, but not installed in the respective one of the plurality of drug product packaging systems 130*a*, 130*b*, and 5) an amount of time since the respective one of the plurality of drug product packaging systems has been used to package the one or more drug products. In some embodiments in which the dispensing canisters can be registered with all of the drug product packaging systems 130*a*, 130*b*, the criterion in which an amount of the one or more drug products that is contained in at least one dispensing canister, respectively, that is associated with, but not installed in the respective one of the plurality of drug product packaging systems 130*a*, 130*b* may not be used. This is because uninstalled canisters may be candidates for installation in any of the drug product packaging systems 130a, 130b and, therefore, may not distinguish between various ones of the drug product packaging systems 130a, 130b.

In some embodiments, the criteria may be evaluated in a sequential order until a difference is determined between one of the drug product packaging systems 130a, 130b and all remaining ones of the drug product packaging systems 130a, 130b. For example, the criteria could be evaluated in the order listed above in which case a determination would be made with respect to which of the plurality of drug product packaging systems 130a, 130b is idle or active. If only one of the drug product packaging systems 130a, 130b is idle, then the evaluation would terminate with the idle drug product packaging system being the recommended system for packaging the one or more drug products. Otherwise, the process would continue by evaluating each criterion in the defined order in an attempt to exclude all of the drug packaging systems 130a, 130b except for one. The sequential order in which the criteria are evaluated may be determined by assigning a priority order to the various criteria, which may be configured through user input via the user interface 340.

In other embodiments, the multiple ones or all of the criteria may be evaluated with weights applied to various ones of the criteria. The criteria for which differences are determined between the ones of the drug product packaging systems 130a, 130b may then be used to compute scores based on the weights associated with those criteria for various drug product packaging systems 130a, 130b. A drug product packaging system 130a, 130b having the highest score, for example, may be recommended for packaging the one or more drug products. Alternatively, the criteria may not be assigned individual weights and a drug product packaging system 130a, 130b that satisfies the most criteria in a desired fashion may be recommended for packaging the one or more drug products.

If application of the criteria does not result in the differentiation of a single drug product packaging system 130a, 130b from all the other ones of the drug product packaging systems 130a, 130b, then one of the drug product packaging systems 130a, 130b remaining after application of the criteria (i.e., not excluded by the criteria) may be selected at random.

Figure 5:
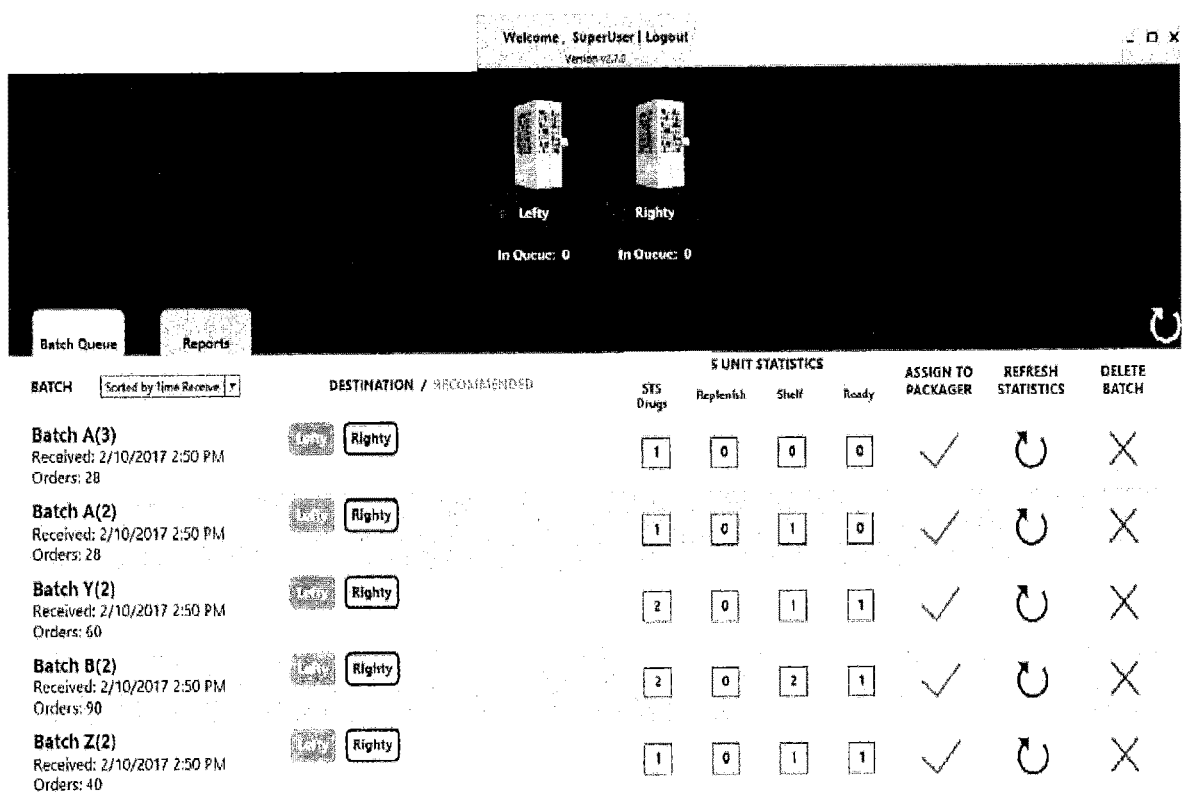
FIG. 5 is a diagram of a user interface for presenting to a user recommendations for assigning drug product packaging orders to drug product packaging systems and receiving input from a user in accordance with some embodiments of the inventive concept.

Returning to FIG. 4, operations continue at block 420 where one of the plurality of drug product packaging systems 130a, 130b is identified as a recommendation for packaging the one or more drug products based on evaluating the at least one criterion. The recommendation may be provided to a user 150 through a graphical user interface at block 425 as shown in FIG. 5. In some embodiments, a default operational mode may be selected and the recommended packaging assignment may be selected automatically and routed to the appropriate drug product packaging system 130a, 130b without any input from the user with respect to the particular packaging order(s). In other embodiments, the user may review and accept or override the recommendation provided through the graphical user interface. In the example illustrated in FIG. 5, two drug product packaging systems are defined with the names "Lefty" and "Righty." Several orders for drug products have been received and grouped together in the form of batches. In the example shown, all of the batches have been recommended for assignment to Lefty with the results from the evaluation of four different criteria shown. The STS drugs criterion corresponds to the criterion of one or more drug products that does not have a dispensing canister associated therewith for the respective drug product packaging system, the replenish criterion corresponds to the criterion of an amount of one or more drug products that is contained in at least one dispensing canister for the respective drug product packaging system, the shelf criterion corresponds to the criterion of an amount of one or more drug products that is contained in at least one dispensing canister that is associated with, but is not installed in, the respective drug product packaging system, and the ready criterion corresponds to the idle or active status for the respective drug product packaging system. As shown in FIG. 5, the user may have the option of confirming the assignment to the recommended drug product packaging system or overriding the recommendation and assigning to a different drug product packaging system by clicking on the desired drug product packaging system underneath the "Destination/Recommended" column. The user may also refresh the evaluation of the criterion to get up to date data or delete a batch of orders from being assigned for packaging. Returning to FIG. 4, the packaging order is assigned to the recommended drug product packaging system 130a, 130b or an alternative drug product packaging system 130a, 130b that is selected by the user at block 430.

Typically, in conventional drug product packaging systems, once a packaging order is assigned to a drug product packaging system the packaging order must be fulfilled on that drug product packaging system and cannot be reassigned. According to some embodiments of the inventive concept, a packaging order(s) that is assigned for fulfillment to one of the drug product packaging systems 130a, 130b may be reassigned to a different one of the drug product packaging systems 130a, 130b. This functionality may be useful, for example, if the user, e.g., pharmacist, pharmacy technician, or the like, wishes to change the assignment, the drug product inventory in the canister installed in the assigned drug product packaging system 130a, 130b changes after the order has been assigned but before the order is fulfilled, one or more of the evaluation criteria in determining a recommended drug product packaging system 130a, 130b for fulfilling the order has changed, and/or a failure in the assigned drug product packaging system 130a, 130b. Thus, a determination is made at block 435 whether the packaging order(s) should be reassigned. If so, then operations continue at block 415 where the criteria for fulfilling the packaging order are evaluated to determine an alternative drug product packaging system 130a, 130b for fulfilling the packaging order(s). Otherwise, operations continue at block 440 where the packaging order(s) is packaged by the assigned drug product packaging system 130a, 130b.

As described above, embodiments of the inventive concept may provide a common database management system that may be used to manage records for multiple drug product packaging systems. The common database management system may allow for centralized routing of drug product packaging orders in an efficient manner based on defined routing criteria. In addition, the common database management system may allow for productivity reports, billing reports, and the like to be generated for an entire facility encompassing multiple drug product packaging systems without the need to separately aggregate the reports from individual packaging systems. Inventory management may also be improved as drug product dispensing canisters may be registered with multiple drug product packaging systems for use therein allowing the canisters to migrate between packaging systems without corrupting inventory data as all inventory data for the multiple packaging systems is managed through the same database management system.

Further Definitions and Embodiments

In the above-description of various embodiments of the present disclosure, aspects of the present disclosure may be illustrated and described herein in any of a number of patentable classes or contexts including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "circuit," "module," "component," or "system." Furthermore, aspects of the present disclosure may take the form of a computer program product comprising one or more computer readable media having computer readable program code embodied thereon.

Any combination of one or more computer readable media may be used. The computer readable media may be a computer readable signal medium or a computer readable storage medium. A computer readable storage medium may be, for example, but not limited to, an electronic, magnetic, optical, electromagnetic, or semiconductor system, apparatus, or device, or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), an appropriate optical fiber with a repeater, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device. Program code embodied on a computer readable signal medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable instruction execution apparatus, create a mechanism for implementing the functions/acts specified in the flowchart and/or block diagram block or blocks.

These computer program instructions may also be stored in a computer readable medium that when executed can direct a computer, other programmable data processing apparatus, or other devices to function in a particular manner, such that the instructions when stored in the computer readable medium produce an article of manufacture including instructions which when executed, cause a computer to implement the function/act specified in the flowchart and/or block diagram block or blocks. The computer program instructions may also be loaded onto a computer, other programmable instruction execution apparatus, or other devices to cause a series of operational steps to be performed on the computer, other programmable apparatuses or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods, and computer program products according to various aspects of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular aspects only and is not intended to be limiting of the disclosure. As used herein, the singular forms "a", "an" and "the" are intended to include the plural forms as well, unless the context clearly indicates otherwise. It will be further understood that the terms "comprises," "comprising," "include", "including", "includes", "have", "has", "having", or variants thereof when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Like reference numbers signify like elements throughout the description of the figures.

It will also be understood, that, although the terms first, second, etc. may be used herein to describe various elements, these elements should not be limited by these terms. These terms are only used to distinguish one element from another.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The aspects of the disclosure herein were chosen and described in order to best explain the principles of the disclosure and the practical application, and to enable others of ordinary skill in the art to understand the disclosure with various modifications as are suited to the particular use contemplated.

What is claimed is:

1. A method comprising:
   performing by a processor:
   providing a database that contains records corresponding to a plurality of drug product packaging systems, each of the plurality of drug product packaging systems being configured to package drug product using a same package type, the records in the database being accessible through a common database management system;
   receiving a packaging order for at least one drug product;
   evaluating a plurality of criteria for fulfilling the packaging order;
   identifying one of the plurality of drug product packaging systems to package the at least one drug product based on evaluating the plurality of criteria; and
   registering a same spare dispensing canister with each of the plurality of drug product packaging systems;
   wherein the plurality of criteria comprises operational status information for each of the plurality of drug product packaging systems, inventory status information for the at least one drug product for each of the plurality of drug product packaging systems, and historical usage information in packaging the at least one drug product for each of the plurality of drug product packaging systems.

2. The method of claim 1, wherein the plurality of drug product packaging systems are configured to package the at least one drug product in pouches formed in a container strip or in a vial.

3. The method of claim 1, wherein receiving the packaging order comprises:
   placing the packaging order in a queue comprising a plurality of packaging orders; and
   selecting the packaging order from the queue based on a priority assigned to the packaging order or a length of time the packaging order has been in the queue;
   wherein evaluating the plurality of criteria comprises evaluating the plurality of criteria for fulfilling the packaging order that was selected.

4. The method of claim 1, further comprising assigning a plurality of weights to the plurality of criteria, respectively;
   wherein evaluating the plurality of criteria for fulfilling the packaging order comprises applying each of the plurality of criteria to the plurality of drug product packaging systems; and
   wherein identifying one of the plurality of drug product packaging systems to package the at least one drug product comprises identifying one of the plurality of drug product packaging systems based on weights corresponding to any ones of the plurality of criteria for which a difference is determined between the ones of the plurality of drug product packaging systems.

5. The method of claim 1, wherein the operational status information for each of the plurality of drug product packaging systems comprises an idle or active status for each of the plurality of drug product packaging systems;
   wherein the inventory status information for the at least one drug product for each of the plurality of drug product packaging systems comprises a number of the at least one drug product that does not have a dispensing canister associated therewith for each of the plurality of drug product packaging systems, an amount of the at least one drug product that is contained in at least one dispensing canister, respectively, for each of the plurality of drug product packaging systems, or an amount of the at least one drug product that is contained in at least one dispensing canister, respectively, that is associated with, but not installed in each of the plurality of drug product packaging systems; and
   wherein the historical usage information in packaging the at least one drug product for each of the plurality of drug product packaging systems comprises an amount of time since each of the plurality of drug product packaging systems has been used to package the at least one drug product.

6. The method of claim 1, wherein evaluating the plurality of criteria for fulfilling the packaging order comprises applying the plurality of criteria to the plurality of drug product packaging systems in a sequential order until a difference is determined between one of the plurality of drug product packaging systems and all other ones of the plurality of drug product packaging systems based on one of the plurality of criteria; and
   wherein identifying one of the plurality of drug product packaging systems to package the at least one drug product comprises identifying one of the plurality of drug product packaging systems based on the one of the plurality of criteria for which the difference is determined between the ones of the plurality of drug product packaging systems.

7. The method of claim 6, further comprising assigning a plurality of priorities to the plurality of criteria, respectively;

wherein the sequential order is based on the plurality of priorities.

8. A system, comprising:
a processor; and
a memory coupled to the processor and comprising computer readable program code embodied in the memory that is executable by the processor to perform operations comprising:
providing a database that contains records corresponding to a plurality of drug product packaging systems, each of the plurality of drug product packaging systems being configured to package drug product using a same package type, the records in the database being accessible through a common database management system;
receiving a packaging order for at least one drug product;
evaluating a plurality of criteria for fulfilling the packaging order;
identifying one of the plurality of drug product packaging systems to package the at least one drug product based on evaluating the plurality of criteria; and
registering a same spare dispensing canister with each of the plurality of drug product packaging systems;
wherein the plurality of criteria comprises operational status information for each of the plurality of drug product packaging systems, inventory status information for the at least one drug product for each of the plurality of drug product packaging systems, and historical usage information in packaging the at least one drug product for each of the plurality of drug product packaging systems.

9. The system of claim 8, wherein the plurality of drug product packaging systems are configured to package the at least one drug product in pouches formed in a container strip or in a vial.

10. The system of claim 8, wherein receiving the packaging order comprises:
placing the packaging order in a queue comprising a plurality of packaging orders; and
selecting the packaging order from the queue based on a priority assigned to the packaging order or a length of time the packaging order has been in the queue;
wherein evaluating the plurality of criteria comprises evaluating the plurality of criteria for fulfilling the packaging order that was selected.

11. The system of claim 8, wherein the operations further comprise assigning a plurality of weights to the plurality of criteria, respectively;
wherein evaluating the plurality of criteria for fulfilling the packaging order comprises applying each of the plurality of criteria to the plurality of drug product packaging systems; and
wherein identifying one of the plurality of drug product packaging systems to package the at least one drug product comprises identifying one of the plurality of drug product packaging systems based on weights corresponding to any ones of the plurality of criteria for which a difference is determined between the ones of the plurality of drug product packaging systems.

12. The system of claim 8, wherein the operational status information for each of the plurality of drug product packaging systems comprises an idle or active status for each of the plurality of drug product packaging systems;
wherein the inventory status information for the at least one drug product for each of the plurality of drug product packaging systems comprises a number of the at least one drug product that does not have a dispensing canister associated therewith for each of the plurality of drug product packaging systems, an amount of the at least one drug product that is contained in at least one dispensing canister, respectively, for each of the plurality of drug product packaging systems, or an amount of the at least one drug product that is contained in at least one dispensing canister, respectively, that is associated with, but not installed in each of the plurality of drug product packaging systems; and
wherein the historical usage information in packaging the at least one drug product for each of the plurality of drug product packaging systems comprises an amount of time since each of the plurality of drug product packaging systems has been used to package the at least one drug product.

13. The system of claim 8, wherein evaluating the plurality of criteria for fulfilling the packaging order comprises applying the plurality of criteria to the plurality of drug product packaging systems in a sequential order until a difference is determined between one of the plurality of drug product packaging systems and all other ones of the plurality of drug product packaging systems based on one of the plurality of criteria; and
wherein identifying one of the plurality of drug product packaging systems to package the at least one drug product comprises identifying one of the plurality of drug product packaging systems based on the one of the plurality of criteria for which the difference is determined between the ones of the plurality of drug product packaging systems.

14. The system of claim 13, wherein the operations further comprise assigning a plurality of priorities to the plurality of criteria, respectively;
wherein the sequential order is based on the plurality of priorities.

15. A computer program product comprising:
a tangible computer readable storage medium comprising computer readable program code embodied in the medium that is executable by a processor to perform operations comprising:
providing a database that contains records corresponding to a plurality of drug product packaging systems, each of the plurality of drug product packaging systems being configured to package drug product using a same package type, the records in the database being accessible through a common database management system;
receiving a packaging order for at least one drug product;
evaluating a plurality of criteria for fulfilling the packaging order;
identifying one of the plurality of drug product packaging systems to package the at least one drug product based on evaluating the plurality of criteria; and
registering a same spare dispensing canister with each of the plurality of drug product packaging systems;
wherein the plurality of criteria comprises operational status information for each of the plurality of drug product packaging systems, inventory status information for the at least one drug product for each of the plurality of drug product packaging systems, and historical usage information in packaging the at least one drug product for each of the plurality of drug product packaging systems.

16. The computer program product of claim 15, wherein receiving the packaging order comprises:
placing the packaging order in a queue comprising a plurality of packaging orders; and selecting the packaging order from the queue based on a priority assigned to the packaging order or a length of time the packaging order has been in the queue;

wherein evaluating the plurality of criteria comprises evaluating the plurality of criteria for fulfilling the packaging order that was selected.

17. The computer program product of claim 15, wherein the operations further comprise assigning a plurality of weights to the plurality of criteria, respectively;

wherein evaluating the plurality of criteria for fulfilling the packaging order comprises applying each of the plurality of criteria to the plurality of drug product packaging systems; and wherein identifying one of the plurality of drug product packaging systems to package the at least one drug product comprises identifying one of the plurality of drug product packaging systems based on weights corresponding to any ones of the plurality of criteria for which a difference is determined between the ones of the plurality of drug product packaging systems.

18. The computer program product of claim 15, wherein the operational status information for each of the plurality of drug product packaging systems comprises an idle or active status for each of the plurality of drug product packaging systems;

wherein the inventory status information for the at least one drug product for each of the plurality of drug product packaging systems comprises a number of the at least one drug product that does not have a dispensing canister associated therewith for each of the plurality of drug product packaging systems, an amount of the at least one drug product that is contained in at least one dispensing canister, respectively, for each of the plurality of drug product packaging systems, or an amount of the at least one drug product that is contained in at least one dispensing canister, respectively, that is associated with, but not installed in each of the plurality of drug product packaging systems; and wherein the historical usage information in packaging the at least one drug product for each of the plurality of drug product packaging systems comprises an amount of time since each of the plurality of drug product packaging systems has been used to package the at least one drug product.

19. The computer program product of claim 15, wherein evaluating the plurality of criteria for fulfilling the packaging order comprises applying the plurality of criteria to the plurality of drug product packaging systems in a sequential order until a difference is determined between one of the plurality of drug product packaging systems and all other ones of the plurality of drug product packaging systems based on one of the plurality of criteria; and wherein identifying one of the plurality of drug product packaging systems to package the at least one drug product comprises identifying one of the plurality of drug product packaging systems based on the one of the plurality of criteria for which the difference is determined between the ones of the plurality of drug product packaging systems.

20. The computer program product of claim 19, wherein the operations further comprise assigning a plurality of priorities to the plurality of criteria, respectively;

wherein the sequential order is based on the plurality of priorities.

* * * * *